Figure 1:
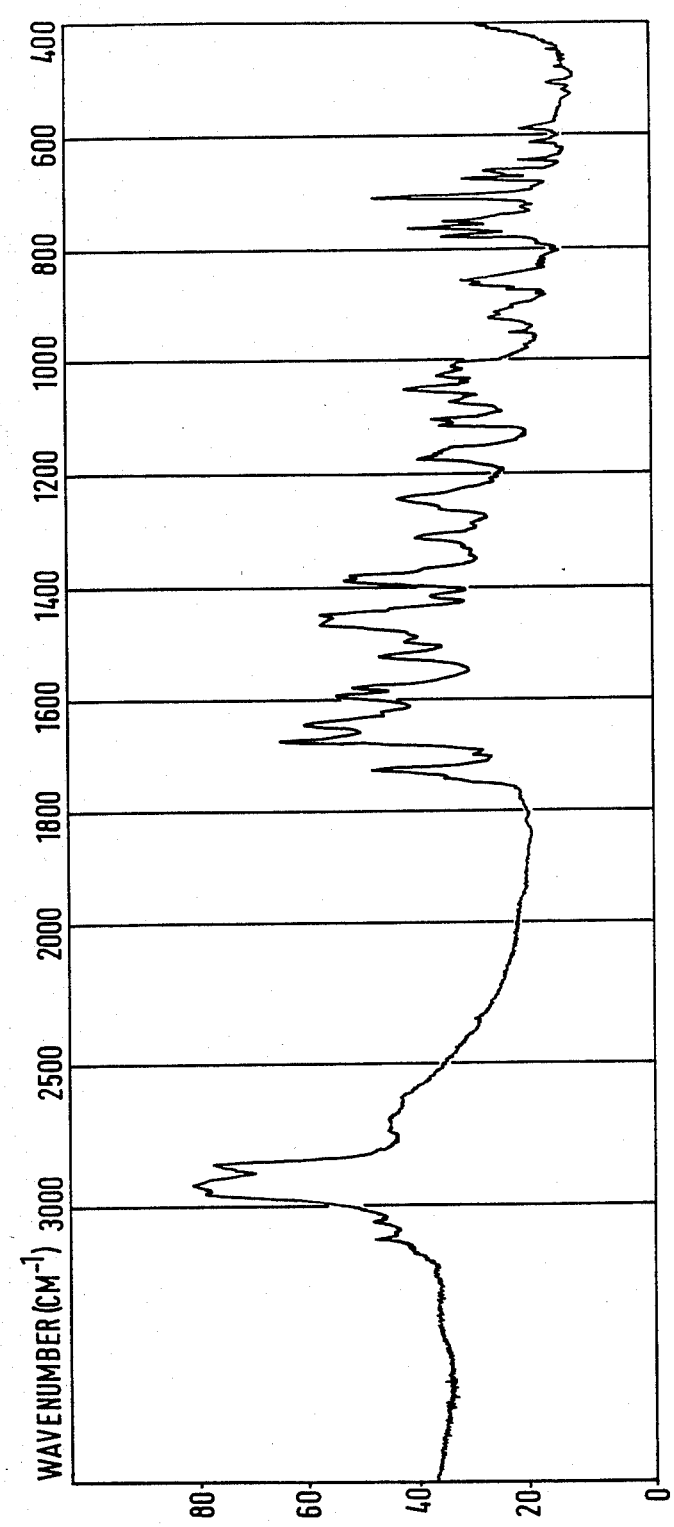

United States Patent [19]

Strachan et al.

[11] Patent Number: 4,510,312
[45] Date of Patent: Apr. 9, 1985

[54] MANUFACTURE OF ANTIBIOTICS

[75] Inventors: William S. Strachan, Montrose, Scotland; Alastair C. Brodie, Ickenham, England

[73] Assignee: Glaxo Group Limited, London, England

[21] Appl. No.: 441,249

[22] Filed: Nov. 12, 1982

[30] Foreign Application Priority Data

Nov. 13, 1981 [GB] United Kingdom ............... 8134359

[51] Int. Cl.³ .......................................... C07D 277/38
[52] U.S. Cl. ...................................... 548/194; 544/25
[58] Field of Search ........................................ 548/194

[56] References Cited

U.S. PATENT DOCUMENTS

| 4,098,888 | 7/1978 | Ochiai et al. | 424/243 |
|---|---|---|---|
| 4,152,432 | 5/1979 | Heymes et al. | 424/246 |
| 4,166,115 | 8/1979 | Takaya et al. | 424/246 |
| 4,258,041 | 3/1981 | O'Callaghan et al. | 424/246 |
| 4,288,434 | 9/1981 | Heymes | 424/246 |
| 4,294,960 | 10/1981 | Takaya et al. | 544/22 |

Primary Examiner—Robert Gerstl
Attorney, Agent, or Firm—Bacon & Thomas

[57] ABSTRACT

The invention provides crystalline ethyl (Z)-2-hydroxyimino-2-(2-triphenylmethylaminothiazol-4-yl)acetate hydrochloride N,N-dimethylformamide solvate which is of value as an intermediate in the preparation of β-lactam antibiotics such as ceftazidime, azthreonam, cefmenoxime, cefotaxime, ceftriaxon, ceftizoxime and cefodizime.

8 Claims, 2 Drawing Figures

MANUFACTURE OF ANTIBIOTICS

This invention relates to improvements in or relating to the manufacture of antibiotics. More particularly it relates to a new compound that is of value in the synthesis of certain β-lactam antibiotics, for example, cephalosporins and 2-oxoazetidines.

A number of antibiotic compounds are now known which have a 2-(2-aminothiazol-4-yl)-2-(substituted oxyimino)acetamido side-chain e.g. in the 7-position of cephalosporins. One such antibiotic, (6R,7R)-7-[(Z)-2-(2-aminothiazol-4-yl)-2-(2-carboxyprop-2-oxyimino)-acetamido]-3-(1-pyridiniummethyl)ceph-3-em-4-carboxylate, hereinafter called "ceftazidime" is described, inter alia, in our U.S. Pat. No. 4,258,041 and details of its preparation are given therein.

One general method for preparing ceftazidime involves building up the 7-position side chain through a series of reactions to form the side-chain acid or a reactive derivative thereof followed by coupling with the 7β-amino cephalosporin nucleus. A series of such reactions for the preparation of a protected form of the 7-side-chain is described in Preparations 1 to 4 of the above-mentioned U.S. patent specification.

We have now found that it is possible to prepare an N,N-dimethylformamide (DMF) solvate of one of the intermediates that is of value in the preparation of β-lactam antibiotics e.g. ceftazidime.

Viewed from one aspect, therefore, the invention provides crystalline ethyl (Z)-2-hydroxyimino-2-(2-triphenylmethylaminothiazol-4-yl)acetate hydrochloride N,N-dimethylformamide (DMF) solvate.

Ethyl (Z)-2-hydroxyimino-2-(2-triphenylmethylaminothiazol-4-yl)acetate hydrochloride in non-solvated form is described in the above-mentioned U.S. patent specification.

We have found the new DMF solvate to be of improved quality and to provide a number of advantages on a manufacturing scale over the unsolvated compound. Use of the unsolvated compound involves very slow filtrations, the need for large volumes of solvent to wash the filter cake and a rather difficult drying process. These factors which slow down the whole procedure and complicate routine manufacture are substantially obviated using the compound of the present invention. The new solvated compound, which is consistently obtained in crystalline form, filters readily and can easily be washed and dried. Use of the solvate renders the process suitable for routine production in contrast to the use of the unsolvated compound. Overall, the new solvate is of considerable advantage in manufacturing terms.

The crystalline DMF solvate according to the invention has been characterised by its X-ray powder diffraction pattern. X-ray crystallographic data in respect of the solvate are given in the following Table.

All 'd' values are given in Ångstrom units and were taken from the CoKα exposure for the higher 'd' spacings and the CuKα exposure for the lower (3 Å) 'd' spacings.

| 'd' (Å) | Intensity | 'd' (Å) | Intensity |
|---------|-----------|---------|-----------|
| 12.62 | vs | 4.05 | s |
| 9.24 | m | 3.97 | s |
| 8.31 | m | 3.75 | m |
| 7.96 | w | 3.63 | s |
| 7.67 | w | 3.41 | ms |
| 7.04 | w | 3.18 | m |
| 6.27 | s | 3.10 | m |
| 6.06 | m | 3.02 | w |
| 5.79 | w | 2.90 | w |
| 5.46 | s | 2.82 | w |
| 4.77 | w | 2.69 | vw |
| 4.59 | w | 2.56 | wd |
| 4.44 | vs | 2.37 | vw |
| 4.35 | s | 2.15 | w |
| 4.15 | w | 1.99 | w | s = strong, m = medium, w = weak, d = diffuse, v = very.

The new solvate according to the invention has also been characterised by its infrared spectrum in a Nujol mull and this is shown in FIG. 1 of the accompanying drawings.

In the new solvate, each mole of ethyl (Z)-2-hydroxyimino-2-(2-triphenylmethylaminothiazol-4-yl)acetate hydrochloride will generally be associated with up to 3, for example from 1 to 3 moles of DMF. The product is normally isolated substantially as the bis-solvate, i.e. containing about 2 moles of DMF, which is a preferred embodiment.

Figure 2:
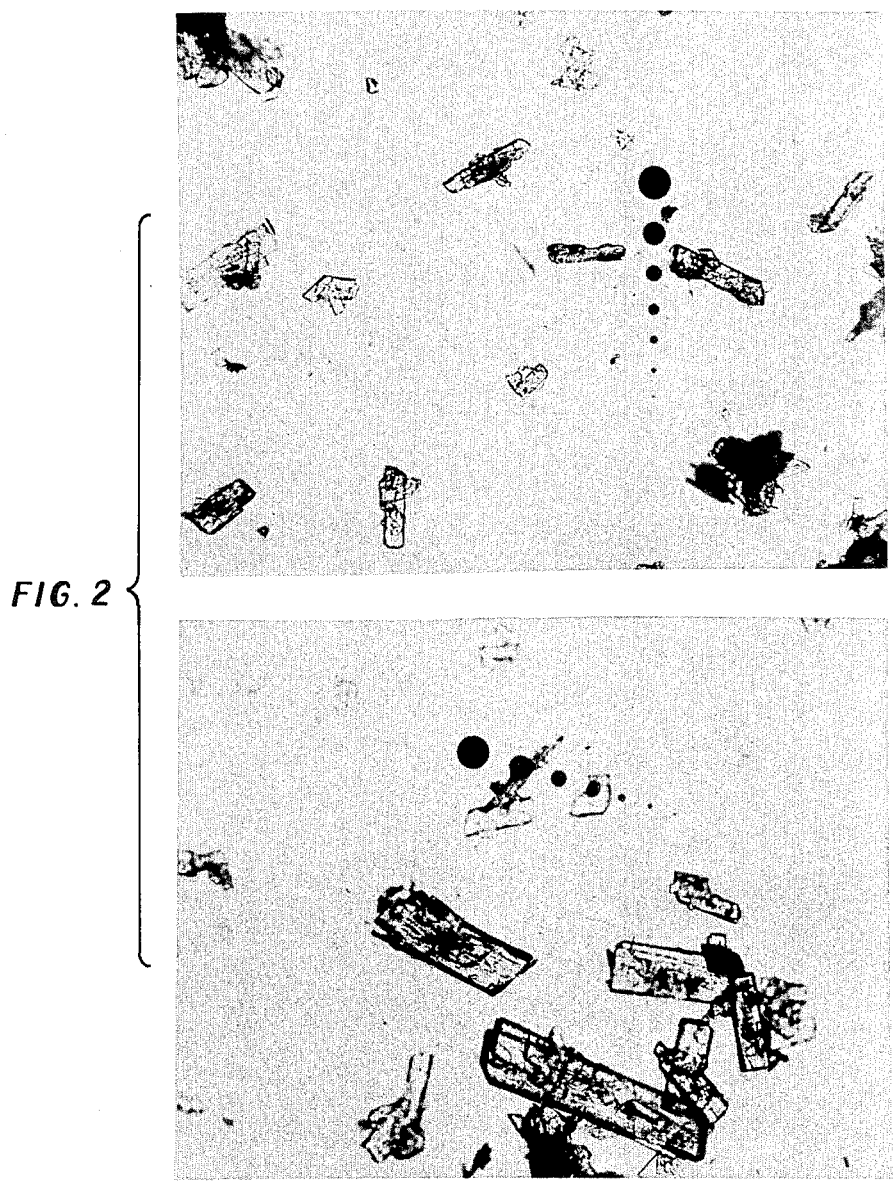

We have found the crystals of the new solvate to have a well defined regular shape e.g. as shown in FIG. 2 of the accompanying drawings, which shows crystals at 185× magnification, and generally the compound is a free flowing particulate material.

According to another aspect of the invention, we provide a process for the preparation of an N,N-dimethylformamide solvate of the invention which comprises precipitating the desired product from a solution comprising ethyl (Z)-2-hyroxyimino-(2-triphenylmethylaminothiazol-4-yl)acetate hydrochloride and DMF.

Precipitation of the DMF solvate generally occurs spontaneously. The DMF used for the precipitation is preferably substantially anhydrous. In order to maximise the yield, precipitation may be substantially completed by addition of an organic solvent, such as di-isopropyl ether in which the DMF solvate is less soluble. The volume of added organic solvent may advantageously be greater than the initial volume of DMF employed in the precipitation. It will be realised that the solvent can either be added to the reaction mixture or vice versa. The precipitation of the solvate may conveniently be effected at around room temperature or slightly above, e.g. at from 0° to 40° C. The ethyl (Z)-2-hydroxyimino-2-(2-triphenylmethyl aminothiazol-4-yl)-acetate hydrochloride from which the solvate may be prepared may be formed in a variety of ways, one of which involves the tritylation using, for example, triphenylmethyl chloride, of the corresponding 2-aminothiazol-4-yl compound. Such a tritylation may if desired be carried out in dimethylformamide in which case the organic solvent, e.g. diisopropyl ether may be added directly to the reaction mixture or vice versa. The ethyl (Z)-2-(2-aminothiazol-4-yl)-2-hydroxyiminoacetate may be prepared as described in U.S. Pat. No. 4,258,041.

We have found that the solvate of the invention may be subsequently processed with great ease to complete the 7β-position side chain acid it is desired to form. Methods by which the 7-side chain found in ceftazidime may be prepared are described in our above-mentioned U.S. patent specification. The same side-chain acid used to prepare ceftazidime may also be used for the preparation of the monocyclic β-lactam azthreonam, which is described in UK Patent Specification No. 2071650A. The solvate of the invention may also be converted into other etherified oxyimino compounds such as ethyl (Z)-2-(2-aminothiazol-4-yl)-2-methoxyiminoacetate as described in British Patent Specification No. 1,581,854. This compound may then be further processed to give the 7β-side chain acid used in the preparation of such cephalosporins as cefotaxime, cefmenoxime, ceftriaxon, ceftizoxime and cefodizime.

The invention will now be more particularly described in the following non-limiting Examples. All temperatures are in °C.

Ethyl (Z)-2-hydroxyimino-2-(2-triphenylmethylaminothiazol-4-yl)acetate hydrochloride N,N-dimethylformamide solvate

EXAMPLE 1

A mixture of ethyl (Z)-2-(2-aminothiazol-4-yl)-2-hydroxyiminoacetate (30 g) and triphenylmethyl chloride (39.0 g) were stirred in dry N,N-dimethylformamide (96 ml) at ambient temperature. After 2.5 hr., during which time the temperature rose to 30°–35° for a short time, the reaction mixture was slowly added to stirred di-isopropyl ether (180 ml). The slurry was filtered and the solid washed with di-isopropyl ether (150 ml) and dried to give the title compound (B 73.77 g) shown by gas chromatography to contain 17.8% w/w N,N-dimethylformamide.

EXAMPLE 2

A mixture of ethyl (Z)-2-(2-aminothiazol-4-yl)-2-hydroxyiminoacetate (15 kg) and triphenylmethyl chloride (19.5 kg) were stirred in N,N-dimethylformamide (48.1) containing 0.05% water, at ambient temperature for 3 hours 50 minutes. Di-isopropyl ether (75 l) was added to the stirred reaction mixture. The slurry was stirred for 20 minutes and filtered. The cake was washed with di-isopropyl ether (50 l) and dried at 40° over 20 hours to give the title compound (40.15 kg) shown by gas chromatography to contain 22.6% N,N-dimethylformamide. Water content (Karl Fischer) 0.1%. I.r. 3120 and 3050 (aminothiazole ring C—H), 3200–2100 (—OH and —NH$_2$), 1725 (ester C=O), and 1670 and 1640 (DMF —CON=) cm$^{-1}$.

A sample prepared by an essentially similar method gave the following n.m.r. characteristics: τ 0.14 (broad s, oxime—OH), 1.92 (broad s, —NH), 2.74 (s, triphenylmethyl protons), 3.15 (s, aminothiazole ring protons), 5.90 (q, J 7 Hz, —COOCH$_2$CH$_3$), 8.84 (t, J 7 Hz —COOCH$_2$CH$_3$), 2.09, 7.13 and 7.29 (s, DMF).

EXAMPLE 3

Trityl chloride (27.9 g) was dissolved in N,N-dimethylformamide (130 ml) at room temperature and a solution of ethyl (Z)-2-(2-aminothiazol-4-yl)-2-hydroxyiminoacetate (21.5 g) in N,N-dimethylformamide (70 ml) added over 2 min. The stirred mixture was kept at room temperature for 67 h. and the solid product isolated by suction filtration then washed with di-isopropyl ether (twice 50 ml) and diethyl ether (twice 50 ml). After drying in vacuo for 3 h. at 40° the title compound was obtained (36.2 g). The filtrate, including washes, was stirred at room temperature for 24 h. whereupon more solid product precipitated. This was isolated by filtration, washed and dried to give a second crop of the title compound (6.10 g). N.m.r. indicates 1.6 mol DMF, water (by Karl Fischer Method) 0.35%.

EXAMPLE 4

A 250 ml conical flask was charged with ethyl (Z)-2-hydroxyimino-2-(2-triphenylmethylaminothiazol-4-yl)acetate hydrochloride (29 g) and N,N-dimethylformamide (93 ml). The mixture was stirred magnetically and a clear solution resulted, quickly followed by precipitation of a crystalline solid. After a total of twenty minutes stirring at ambient temperature, the solid was collected by vacuum filtration washed with N,N-dimethylformamide and dried in vacuo at 40° for 2 hours to give the title compound in a yield of 34.2 g, shown by gas-liquid chromatography to contain 25% m/m (2.25 moles) N,N-dimethylformamide. % H$_2$O (Karl Fischer) 0.4, 0.4; % Cl 5.5 C$_{26}$H$_{24}$ClN$_3$O$_3$S 2.25 DMF requires 5.4% Cl.

We claim:

1. Crystalline ethyl (Z)-2-hydroxyimino-2-(2-triphenylmethylaminothiazol-4-yl)acetate hydrochloride N,N-dimethylformamide solvate.

2. The compound according to claim 1 which exhibits the following X-ray crystallographic data when subjected to an X-ray powder diffraction study using CoKα and CuKα radiation:

| 'd' (Å) | Intensity | 'd' (Å) | Intensity |
| --- | --- | --- | --- |
| 12.62 | vs | 4.05 | s |
| 9.24 | m | 3.97 | s |
| 8.31 | m | 3.75 | m |
| 7.96 | w | 3.63 | s |
| 7.67 | w | 3.41 | ms |
| 7.04 | w | 3.18 | m |
| 6.27 | s | 3.10 | m |
| 6.06 | m | 3.02 | w |
| 5.79 | w | 2.90 | w |
| 5.46 | s | 2.82 | w |
| 4.77 | w | 2.69 | vw |
| 4.59 | w | 2.56 | wd |
| 4.44 | vs | 2.37 | vw |
| 4.35 | s | 2.15 | w |
| 4.15 | w | 1.99 | w | s = strong, m = medium, w = weak, d = diffuse, v = very.

3. The compound according to claim 1 wherein each mole of ethyl (Z)-2-hydroxyimino-2-(2-triphenylmethylaminothiazol-4-yl)acetate hydrochloride is associated with from 1 to 3 moles of N,N-dimethylformamide.

4. The compound according to claim 1 which is substantially the bis-N,N-dimethylformamide solvate of ethyl (Z)-2-hydroxyimino-2-(2-triphenylmethylaminothiazol-4-yl)acetate hydrochloride.

5. The compound according to claim 1 in the form of a free flowing particulate material.

6. A process for the preparation of the compound according to claim 1 which comprises precipitating the desired product from a solution comprising ethyl (Z)-2-hydroxyimino-(2-triphenylmethylaminothiazol-4-yl)acetate hydrochloride and N,N-dimethylformamide.

7. A process according to claim 6 wherein precipitation is substantially completed by addition of an organic solvent in which the desired compound is less soluble than in N,N-dimethylformamide.

8. A process according to either of claims 6 and 7 wherein precipitation is effected at a temperature of from 0° to 40° C.

* * * * *